United States Patent [19]

Nuwayser

[11] Patent Number: 4,810,499

[45] Date of Patent: * Mar. 7, 1989

[54] TRANSDERMAL DRUG DELIVERY SYSTEM AND METHOD

[75] Inventor: Elie S. Nuwayser, Wellesley, Mass.

[73] Assignee: Biotek, Inc., Woburn, Mass.

[ * ] Notice: The portion of the term of this patent subsequent to Nov. 25, 2003 has been disclaimed.

[21] Appl. No.: 152,940

[22] Filed: Feb. 5, 1988

Related U.S. Application Data

[63] Continuation of Ser. No. 920,299, Oct. 17, 1986, abandoned, which is a continuation-in-part of Ser. No. 653,362, Oct. 1, 1984, Pat. No. 4,624,665.

[51] Int. Cl.$^4$ .............................................. A61F 13/02
[52] U.S. Cl. ...................................... 424/448; 424/449
[58] Field of Search ................................ 424/448, 449

[56] References Cited

U.S. PATENT DOCUMENTS 4,460,372  7/1984  Campbell et al. .................... 424/449
4,568,343  2/1986  Leeper et al. ....................... 424/449
4,624,665  11/1986  Nuwayser ............................ 424/448

Primary Examiner—Thurman K. Page
Assistant Examiner—L. R. Horne
Attorney, Agent, or Firm—Crowley, Richard P.

[57] ABSTRACT

A transdermal drug delivery system which system comprises an impervious backing sheet and face membrane, the backing sheet and membrane secured together to form an intermediate reservoir. The face membrane is a macroporous membrane which has pores of sufficient size to avoid any rate control of the drug to be transdermally delivered to the user. The reservoir contains a viscous liquid base material selected to exude from the membrane to form a film and to occlude the skin of the user to force hydration of the stratum corneum with water from the lower layers of the epidermis of the user. The liquid base material contains an effective, therapeutic amount of the drug for transdermal delivery, such as the contraceptive steroid, which drug is highly soluble in the liquid base material. In use, the liquid base material exuded from the macroporous membrane face forms a thermodynamically stable, thin film layer in intimate contact with the skin, while the drug is released from the base material and transdermally into the user.

18 Claims, 2 Drawing Sheets

TRANSDERMAL DRUG DELIVERY SYSTEM AND METHOD

This is a continuation of co-pending application Ser. No. 920,299 filed on Oct. 17, 1986, now abandoned, which is a continuation-in-part of application Ser. No. 653,362, filed Oct. 1, 1984, now U.S. Pat. No. 4,624,665.

BACKGROUND OF THE INVENTION

Transdermal delivery of medication is not a new concept, as a variety of medications that are readily available for delivery through the skin have been available in ointment form for over thirty years. With ointments, however, it is difficult to achieve precise drug dosage. In a transdermal patch system, this problem is eliminated by controlling the rate of drug release over a prescribed period of time. Patches are worn behind the ear, on the chest, or on the arm and dispense a drug for as long as a week at a time. For certain drugs, transdermal delivery has significant advantages over oral administration. It eliminates "first pass" inactivation by the liver and irregular gastric absorption. Because of constant absorption through the skin, it maintains relatively constant blood levels of the drug.

Two drugs, scopolamine and nitroglycerin, have recently become commercially available in transdermal form. Although there are differences in composition and in the mechanism of drug delivery among the available transdermal delivery systems, they all appear to be functionally similar. Generally, the systems have essentially steady state reservoirs sandwiched between an impervious backing and a membrane face. The systems usually are attached to the skin by an adhesive gel. Some products have a rate-controlling outer microporous membrane. One product depends on a diffusion matrix in which nitroglycerin molecules are in equilibrium between lactose crystals and the liquid phase. In another product, micropockets of nitroglycerin are evenly dispersed throughout a silicone polymer which controls the drug release rate and prevents dose dumping.

A description of the different commercial products which deliver nitroglycerin transdermally is set forth by Dasta, et al., *American Pharmacy*, NS22, 2, 29-35, February, 1982, which article also illustrates the various prior art nitroglycerin patches and their construction and operation, and which article is hereby incorporated by reference.

U.S. Pat. No. 4,336,243, issued June 22, 1982 describes transdermal nitroglycerin pads wherein the pad comprises a silicone polymer matrix being a crosslinked silicone rubber having from about 10 to 200 microns microseal compartments formed by the in situ cross-linking of the silicone rubber after it is admixed with a hydrophilic solvent containing the nitroglycerin in a hydrophobic solvent which enhances the dispersion and transport. U.S. Pat. No. 4,053,580, issued Oct. 11, 1977 describes an earlier pharmaceutical delivery device employing a silicone polymer matrix wherein the rate of release of the active ingredient is controlled by altering the solubility of the hydrophilic solvent system for the polymer matrix.

Another polymer diffusion matrix transdermal delivery system is described in published European patent appication 80300038.9, of A. Keith entitled "Polymeric Diffusion Matrix and Method of Preparation and Drug Delivery Device Comprising Said Matrix". This application describes a polymeric diffusion matrix composed of glycerol and polyvinyl alcohol together with a water soluble polymer to provide a polymer matrix capable of sustained release of a drug dispersed in the matrix. Typically, the water soluble polymer comprises a polyvinylpyrrolidone or a water soluble cellulosic derivative. U.S. Pat. No. 3,797,494, issued Mar. 19, 1974 describes a transdermal bandage which includes a reservoir with a drug confined within the interior chamber of the reservoir and distributed throughout a reservoir matrix. In one embodiment, the drug is released by a controlling microporous material, which microporous material meters the flow of the drug into the skin at a controlled rate. In another embodiment, an adhesive coating is uniformly distributed through microcapsules comprising a drug encapsulated with a microporous rate-controlling material.

While many transdermal drug delivery systems have been described as economical and effective, a transdermal drug delivery system, particularly for the delivery of contraceptive steroid drugs, is still needed, and desired, particularly percutaneous delivery of steroid contraceptives in a controlled manner for periods of time ranging from one to four weeks or more.

Levonorgestrel is a synthetic steroid which has powerful progestational activity with minimal side effects at very low doses. Estradiol is a natural estrogen which has limited oral effectiveness because of "first pass" inactivation during circulation. On the other hand, the synthetic steroid, ethinylestradiol, is active orally, since its inactivation by the liver and other tissues is very low. These contraceptives and others, like Mestranol, Norethindrone, etc., are employed in various oral contraceptives manufactured in this country. Although levonorgestrel pills contain 150 micrograms of the drug, studies with implantable drug delivery systems indicate that only 30 micrograms per day are sufficient to prevent fertility.

Thus, it is desirable to provide an effective transdermal drug delivery system for the transdermal delivery of drugs, particularly contraceptive steroids.

SUMMARY OF THE INVENTION

The invention concerns a transdermal drug delivery system and a method of manufacture and use of such system. In particular, the invention relates to a transdermal drug delivery system particularly useful for the controlled release of a contraceptive steroid drug or a combination of such drugs.

The invention relates to a transdermal drug delivery system which may be employed with a drug which is desired to be delivered transdermally at a controlled or sustained rate, typically a zero order rate or other delivery release patterns as desired. The transdermal drug delivery system of the invention prevents dose dumping of the drug caused by accidental rupture of the retaining member and ensures effective and prolonged delivery of the drug.

The invention relates to a method of and system for the transdermal delivery of drugs into a patient by sealing the skin of the patient with a thin layer of a viscous material to occlude the skin and transporting a desired dosage of a drug across the thin layer. It has been found that the use of solid microparticles suspended in a liquid base material in a reservoir, as in the parent application, is not wholly necessary when the liquid base material has a high solubility of the drug. Specifically, when the drug is highly soluble in the liquid base material, the microparticles become depleted of the drug in storage and thus serve no useful function in the transdermal drug delivery system. It has been discovered that the retention of a liquid base material which serves to occlude the user's skin and which has a high solubility for the drug provides a transdermal system without the need for the microparticles which formerly served to provide a continuous run of drug to the base material. The container system for the liquid base material generally comprises a macroporous, non-rate-controlling face membrane with an impervious backing to form a pool or patch-like system of desired face membrane area with the face of the membrane placed over and in contact with the thin, occluding viscous layer on the skin. The thin viscous layer may be coated or placed on the skin repeatedly and the patch system placed on top of the thin viscous layer or the viscous layer formed in situ by exudation through the membrane face when the patch or pool system is placed in position on the skin. The patch or pool container system generally is retained in a transdermal position by the use of a peripheral adhesive layer about the patch or pool. Typically, the face or transport area of the membrane is covered prior to use by a removable cover such as a peelable strip of impervious sheet material.

In another embodiment, the liquid base material containing a drug for delivery, which drug is highly soluble in the liquid base material, may be suspended in a viscous material and the composition then spread as a layer over the skin of the user with or without a covering or face membrane material.

The system is characterized by a macroporous membrane which delivers a thin liquid film of the base vehicle to the skin and whose function is to deliver the drug to the skin. The function of the viscous liquid material and film is to occlude the skin, causing the stratum corneum to swell and hydrate by forcing the diffusion of water from the lower layers of the epidermis and thus to accelerate the drug delivery. The first phase in transdermal delivery is dependent upon the rate of diffusion of the drug within the vehicle and its rate of release from the vehicle. The drug concentration in the vehicle determines the thermodynamic activity and influences the diffusion of the drug out of the vehicle.

The present drug delivery system wherein the drug is soluble in the base liquid material provides a constant source of the drug. The presence of the drug in the base vehicle helps to maintain a constant thermodynamic activity of the drug by insuring that the concentration of the drug is close to saturation.

The delivery of the base liquid to the skin is regulated by a macroporous membrane (for example, ranging from about 1 to 1000 microns) whose properties and pore size are selected to match those of the base vehicle. A hydrophobic membrane, for example, is best used with a hydrophobic delivery base vehicle, and a hydrophilic membrane with a hydrophilic vehicle, while smaller micron pores, e.g. 50 to 200, deliver a smaller quantity of the vehicle than larger micron pores, e.g. 300 to 600.

The principal barrier to permeation of small molecules through the skin is provided by the stratum corneum, or "horny layer", of cells which is about 10 to 15 microns thick. This layer is composed of a dispersion of hydrophilic proteins in a continuous lipid matrix. The lipid components of the layer which comprise only 20% to 30% of the weight of the tissue are directly responsible for its unique low permeability (Scheuplein, 1971).

The stratum corneum may be regarded as a passive diffusion membrane, albeit not entirely inert, which follows Fick's Law in which the steady state flux Js is:

$$Js = \frac{Km \ D \ Cs}{S}$$

where $Km = \frac{\text{solute sorbed per cc of tissue}}{\text{solute in solution per cc solvent}} = \frac{Cm}{Cs}$ Cs = concentration difference of solute across membrane.

D = average membrane diffusion coefficient for solute.

S = membrane thickness.

Swelling of the corneum can be produced by hygroscopic or other substances if they penetrate the hydrophilic zone or if lipophilic substances penetrate the hydrophobic zones. Increasing the state of hydration increases the porosity and thickness of the layer and favorably influences the transport of the drug by two to threefold. The simplest method for increasing hydration is to occlude the skin which forces the diffusion of water from the lower layers of the epidermis. Estimated diffusion constant for low molecular weight non-electrolyte is $10^{-9}$ cm. sq./sec. for stratum corneum and $10^{-6}$ cm. sq./sec. for the dermis.

The degree of hydration of the stratum corneum is provided by the macroporous membrane which delivers a thin liquid film of the vehicle to its outer surface to occlude the skin. The liquid film is simultaneously in contact with the skin and the liquid or viscous vehicle of the reservoir through the macroporous channels of the membrane. Occlusion of the skin which follows may be influenced by the properties of the vehicle and the membrane.

Following topical administration of many drugs, including steroids like estrogen and norgesterone, a reservoir can form in the skin. The existence of this reservoir and its localization in the stratum corneum was first proven by Vickers (1963). Much of the work in this area has dealt with local action of drugs (e.g., hexachlorophene, sunscreens, cortisol). However, prolonged toxic response following topical administration of vasoconstrictors demonstrates that a cutaneous reservoir can provide sustained release into the systemic circulation. Accumulation of both estrogen and progesterone in subcutaneous tissue and underlying muscle has been observed and is more pronounced with percutaneous than with subcutaneous administration. The duration of the local reservoir appears to be dependent on the normal 14-day cycle of epidermal turnover. Irritation with a detergent or methotrexate increases turnover and can reduce the duration of the reservoir by nearly 50%. Inhibition of turnover with fluorinated steroids can double the duration to 28 days. In addition, a compound which very rapidly penetrates and diffuses is maintained in the reservoir for a short period of time (e.g., nicotine, 3 to 4 days). Since occlusion of the area of application appears necessary to promote sustained absorption from the reservoir, continued absorption following removal of the delivery system should be minimal unless the concentration is very high.

Pronounced and prolonged effects of estrogens and gestagens can be expected by the transdermal route since it is the total amount of hormone absorbed by the body that is decisive, and not the peak height of the hormone level. The flux rates of steroids through human skin has been studied by others and are shown in Table 1.

TABLE 1

Flux Rates of Steroids

| Steroid | Flux (Moles/CM$^2$ HR.) | |
| --- | --- | --- |
| | (Feldman 1969) | (Schaefer 1979) |
| 17$^B$ estradiol | 8.2 × 10$^{-11}$ | 5.8 × 10$^{-10}$ |
| 17$^B$ estradiol | | 4.6 × 10$^{-10}$ |
| Testosterone | 5 × 10$^{-11}$ | 1 × 10$^{-9}$ |
| Estriol | | 7.8 × 10$^{-11}$ |
| Progesterone | 3.4 × 10$^{-11}$ | |
| Hydrocortisone | 2.5 × 10$^{-11}$ | |
| Corticosterone | 7.5 × 10$^{-12}$ | |

Table 1 shows that the flux rates of estradiol and progesterone are fairly high in comparison to the corticosterones. These flux rates depend upon the concentration of the applied substance in the vehicle. At low concentrations, the rates are proportional to the concentration in the vehicle. This proportionality is not 1 to 1 since a doubling of the concentration increases the flux by about 30% to 50%.

This general pattern of regional variation was found to hold for other chemical moieties (steroids, pesticides, and antimicrobials). Although the stratum corneum is generally accepted to be the major barrier to percutaneous penetration, this appears to hold only if the skin is intact. Damage to the stratum corneum makes the other layers function as barriers. For example, the penetration of hydrocortisone through modified skin results in a tenfold increase in the penetration of hydrocortisone from 1% to 10% when the skin is occluded. The thin liquid film which is exuded by the macroporous membrane occludes the skin to increase drug penetration.

The drug delivery system of the invention is based upon the use of a liquid base material which has a high solubility for one or more drugs. The drug is suspended or dissolved in a dermatologically-acceptable, viscous liquid base material or vehicle. The base is separated from the skin by a non-drug, non-rate-controlling macroporous membrane. The outer rim or perimeter of the membrane is covered by a non-sensitizing, hypoallergenic adhesive layer or other means to secure the system to the skin which holds the microporous membrane in contact or adjacent to the skin and prevents loss of the drug to the surrounding area.

An important feature of the drug delivery system is the macroporous retaining membrane which separates the liquid base from the skin. This membrane delivers a thin film, controlled amount of the base material to its outer face surface to contact the skin. The liquid film occludes the skin and forces hydration of the stratum corneum with water from the lower layers of the epidermis. This in turn accelerates delivery of the drug, e.g. steroids, across the stratum corneum. Intimate contact between the skin and the thermodynamically stable, viscous liquid base also ensures uniform delivery of the drug throughout the treatment period. Unlike microporous membranes, the macroporous membrane does not control the rate of drug delivery to the skin, but solely the amount and thickness of the film of liquid material in contact with the skin.

The macroporous membrane ensures the presence of a continuous drug-filled liquid base pathway between the viscous base reservoir and the skin. The dimensions of the macropores and the degree of hydrophobicity of the membrane are selected to match the properties of the liquid base (i.e., viscosity, hydrophobicity). The function of the macroporous membrane is to permit only a small, but sufficient quantity of the base material to pass through the pores to the skin surface without being messy or leaky.

The drugs in the liquid base material provide a thermodynamically stable base with a constant driving force of the drug in the liquid base.

The transdermal drug delivery system of the invention usually includes an impervious backing sheet with a macroporous face membrane, the backing sheet and the macroporous membrane typically secured together generally along its edges to form an intermediate layer-like reservoir therebetween. The macroporous membrane has pores of sufficient size to avoid rate control of the active drug ingredient to be transdermally delivered, but of a size sufficient to permit the liquid base material to be exuded therefrom so as to form a thin film of the base material for intimate contact with the skin of the user adjacent the face of the macroporous membrane.

The reservoir comprises a dermatologically-acceptable, generally viscous liquid base material. The viscosity should be sufficiently high to suspend the microparticles therein and to prevent leakage or excessive flow through the membrane pores, but low enough to permit the function of the thin film on the skin. The liquid base material includes an effective, therapeutic amount of an active drug ingredient or a combination thereof, such as a contraceptive steroid, like levonorgestrel or estradiol or a combination thereof, for transdermal delivery for a particular therapeutic purpose such as contraception. The drug is present in an effective therapeutic amount. Typically, an adhesive layer is placed about the periphery of the drug delivery system and usually an impermeable material, such as a protective peel strip, is secured to the open face of the macroporous membrane, which peel strip is to be removed just prior to use.

In use and upon removing of the peel strip, the drug delivery system in the form of a patch is applied to the skin of the user at a desirable location and the patch adhered by an adhesive exposed after removal of the peel strip. The macroporous nature of the membrane permits the viscous liquid base material in the reservoir to exude through the macropores to form a thin film on the face of the macroporous membrane and places the macroporous membrane in intimate contact with the skin of the user thus forming a thin, thermodynamically stable thin film. The active drug ingredient is released from the base liquid material and transported directly through the viscous liquid base material into the skin of the user.

The drug delivery system of the invention contributes significantly to the accelerated permeation of the drug through the skin, since the skin is continuously in contact with the drug in solution. Further, since the skin is occluded to permit hydration of water from the lower layers, the permeation of the drug from the liquid base material into the hydrated stratum corneum is much faster than when a dry, dehydrated corneum is presented. In addition, the skin is continuously in contact with the viscous liquid base material which is generally selected to have emollient properties. This emollient contributes to the accelerated delivery by maintaining the outer skin softness and pliability to assure continuous contact between the skin, the liquid base material and the membrane surface which is in quite a contrast to contact with a dry solid matrix of the prior art.

The drug in the liquid base produces a thermodynamically-stable liquid base as a source of the active drug. The rate of drug delivery may be modified and tailored by the selection of the viscous liquid base material, composition and properties as to the degree of hydrophilicity or hydrophobicity. The various additives may be compounded and added into the liquid base material, which compounds may be employed to impart special properties to the liquid base material; for example, to enhance diffusion, control steroid reservoir formation, improve antiseptic properties, reduce infection, control viscosity, or to add emollient or lubricant properties where prolonged usage of the transdermal drug delivery system is desired.

The liquid base material may comprise a variety of materials, but typically should be a viscous-type liquid material capable of suspending the plurality of solid microparticles therein and also to be exuded through the selected pores of the macroporous membrane so as to form a thin, thermodynamically stable film on the skin of the user. The liquid base material should be dermatologically-acceptable to the user. The viscosity of the liquid base material should be high enough so that the liquid base material will not run from the macropores of the macroporous membranes and deplete the reservoir or become messy to the user, and yet not high enough to prevent the liquid base material from entering the pores and forming the thin film on the skin of the user after a protective face layer has been peeled away from the other face of the macroporous membrane. Typically, the liquid base material should have a gel or grease-like viscosity and properties.

The liquid base material should be selected to be compatible with and to permit the transport of the drug within the microparticles. Typically, if the drug is a low water soluble-type drug, then the liquid base material would be a low water soluble base material generally matching the hydrophobicity of the drug, and vice versa where the drug is water soluble, the liquid base material may be selected to be also water soluble so that there is transport and compatibility from the drug release through the wall of the microparticle and so the drug may move effectively through the liquid base material in the reservoir and onto the thin film adjacent the user directly into the skin of the user. For example, the liquid base material may comprise a hydrophobic material, such as a long chain, e.g. $C_8$ to $C_{22}$ hydrocarbon-type material, particularly for use with water insoluble or very low water soluble drugs, such as for example, a grease-like hydrocarbon such as a petroleum-based jelly, e.g. vaseline, a semi-solid mixture of hydrocarbons having a mp of 38° C. to 60° C.

The liquid base material may comprise also a hydrophilic-type material, such as polyalkylene polyol, such as polyethylene or polypropylene polyol like polyethylene glycol, glycerol or a water solution placed in a gel-like form through the use of viscosity-modifying additives or gel-like material, such as polyvinylpyrrolidone, agar, proteins, thickeners and the like. In addition, it should be noted that the liquid base material in the reservoir may contain other modifying additives to impart other desirable properties, such as the use of emollients, such as glycols like glycerine, viscosity-controlling agents, preservatives, thickening agents, antibacterial agents, such as quaternary ammonium compound, stabilizers, depletion-indicating devices such as dyes, waxes and other material typically employed in pharmaceutical and cosmetic applications and which are dermatologically and pharmaceutically acceptable.

The macroporous membrane material comprises a sheet material having pores to permit the passage of the viscous liquid base material. The function of the membrane is merely to contain the viscous liquid within the reservoir and to permit a thin film to be formed on the face side of the membrane. The macroporous membrane may be formed of a variety of materials, either synthetic or natural polymeric material, but typically a membrane material as used in the prior art, such as for example, of a cellulosic material, an ethylenevinyl acetate copolymer material, cellulose acetate material, vinyl halides, polyvinyl chloride, nylon, porous polyolefins such as polyethylene, polypropylene and fluorocarbons and other materials which are adapted to be formed with or have pores of controlled size.

The drug in the liquid base material may comprise a varying amount and range, for example, from 5% to 95% by weight, such as 20% to 80% by weight.

The active drug ingredient may comprise a wide variety of materials or combinations and be selected for the particular therapeutic function desired to be transdermally released. Preferably, the active drug ingredient does not react with and is chemically inert with the liquid base material. The drug in the liquid base material, such as a polyol, may include an active drug steroid such as levonorgestrel or estradiol and combinations.

The drug material to be used as the active ingredient may vary and comprise, for example, antibiotics, antibacterial agents, hormones, steroids, or other therapeutic agents. However, the principles of the drug delivery system will be illustrated employing a contraceptive steroid hormone with a drug delivery system designed to provide for sustained release by transdermal delivery of a contraceptive hormone such as levonorgestrel or estradiol. The release of the drug should be such as for an effective amount to be transdermally delivered to the user in an amount to be effective for the purpose for which the drug is selected. For example, with contraceptive steroid hormones, approximately 5 to 150 micrograms per day per user and generally 20 to 50 micrograms per day is sufficient to prevent female fertility when using a levonorgestrel drug as an active ingredient.

The drug delivery system may be in the form of a patch or bandage and wherein the face of the macroporous membrane in contact with the skin through the thin, thermodynamically liquid layer may range as desired depending upon the transport mechanism and rate, but typically would range from about 1 to 30 square centimeters, and more typically 2 to 10 square centimeters.

The invention will be described for the purposes of illustration only in connection with certain embodiments; however, it is recognized that various changes, modifications, additions and improvements may be made to the illustrated embodiments by a person skilled in the art all falling within the spirit and scope of the invention.

DESCRIPTION OF THE EMBODIMENTS

Figure 1:
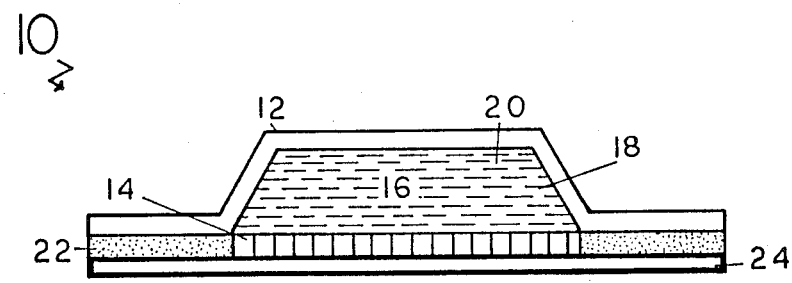
FIG. 1 is a schematic, sectional, illustrative view of the drug delivery patch system of the invention.
Figure 2:
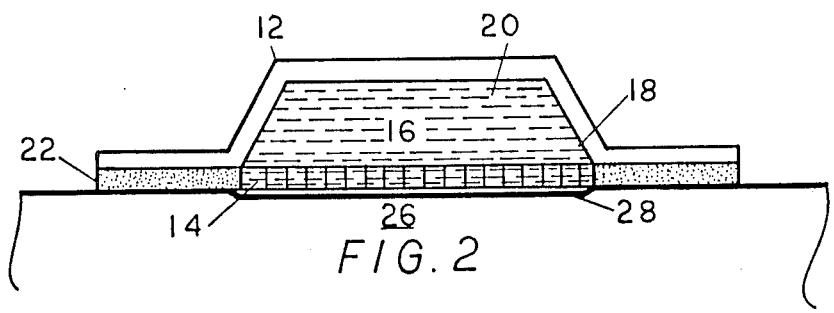
FIG. 2 is a schematic, sectional, illustrative view of the patch delivery system of FIG. 1 as applied to the skin of a user.
Figure 3A:
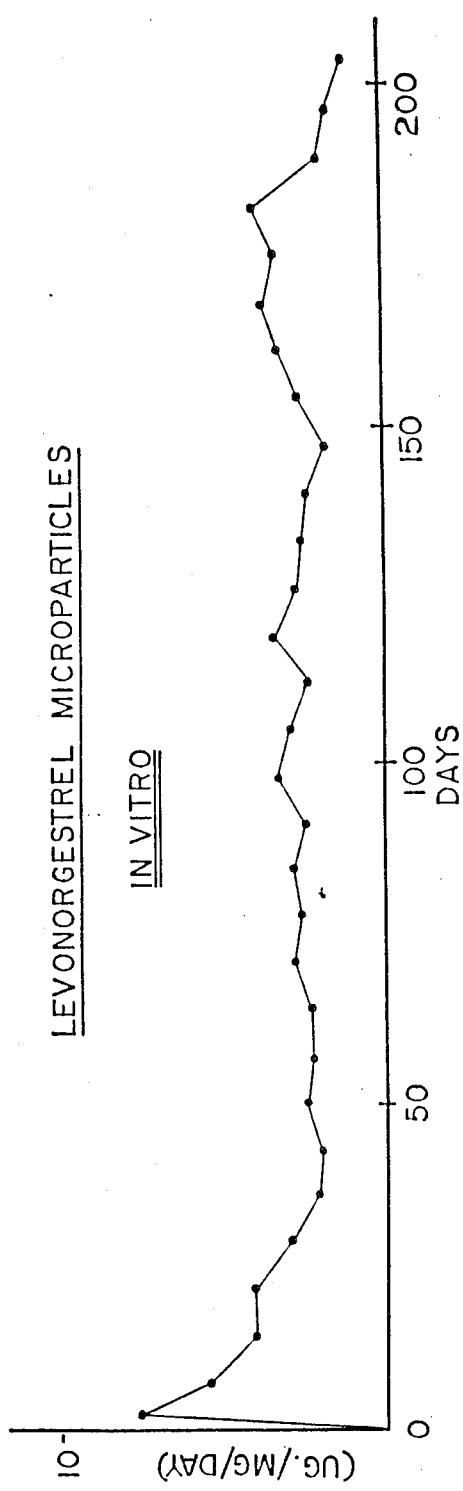
FIG. 3 (a and b) is a graphical representation of the comparison of in vitro release and plasma levels of levonorgestrel from microcapsules.
Figure 3B:
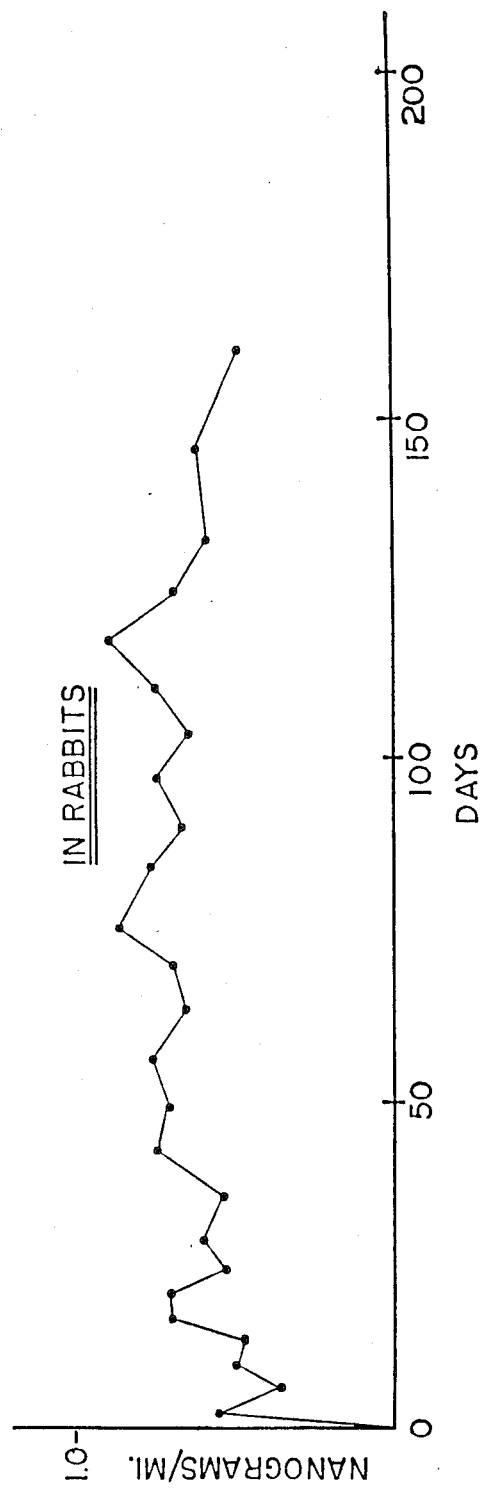

FIGS. 1 and 2 show a bandage-type, transdermal, sustained-release delivery system of the invention 10 wherein the device comprises an impervious backing sheet 12 and a macroporous face membrane 14. The backing sheet 12 and the macroporous membrane 14 form a generally flat reservoir 16 therebetween, the reservoir containing a viscous liquid base material 18 such as a viscous polyethylene glycol vehicle. Uniformly suspended or dissolved in the liquid viscous base is a drug 20, for example, levonorgestrel, in an amount to deliver about 30 micrograms per day of the levonorgestrel over a period of one to four weeks. Around the peripheral edge of the backing material is an adhesive layer 22 while a removable peel strip 24 against the face of the macroporous membrane 14 prevents the discharge of the viscous liquid base material prior to use. FIG. 2 shows the application of the bandage-type delivery system to the skin of a user 26 and illustrates that a thin liquid film 28 of the viscous liquid 18 in the reservoir 16 forms across the entire face of the macroporous membrane 14 to maintain intimate contact between the face of the macroporous membrane 14 in the skin 26 and to accelerate the transdermal delivery of the drug to the user 20.

To illustrate the effect of high solubility of the drug in the base liquid, a dosage form was prepared according to the invention, and contained 0.5 mg of levonorgestrel microparticles (microparticles prepared with levonorgestrel and poly L-lactide of about 200 microns in size and prepared as in the parent applicaion example). The microparticles had a drug loading of 30%, thus the dosage form contained 0.15 mg of levonorgestrel. The microparticles were suspended in 0.5 ml of base liquid vehicle, composed of polyethylene glycol 600. The solubility of levonorgestrel in the vehicle was found to be well in excess of 2 mg/ml. Therefore, on storage, the entire drug content of the microparticles leached into the vehicle. In this case, direct dissolution of the drug in the vehicle would give a dosage form equivalent to one based on a microparticle suspension.

LIST OF REFERENCES

Dasta, J. F. and Geraets, D. R., Topical Nitroglycerin: A New 'Twist to an Old Standby, *Am. Pharm.* NS22 (2), 29 (1982).

Feldman, R. J. and Maibach, H. I., *J. Invest. Derm.* 52, 89 (1969).

Schaefer, H., Stuttgen, G. and Schalla, W., Contraception via Topical Application? - A Review, *Contraception,* 20 (3), 225 (1979).

Scheuplein, R. J. and Blank, I. H., Permeability of the Skin, *Physiol. Rev.* 51, 702 (1971).

Vickers, C. F. H., *Arch. Dermatol.* 88, 20–23 (1963).

What is claimed is:

1. A transdermal drug delivery system, which system comprises:
   (a) an impervious backing sheet;
   (b) a macroporous liquid base retaining face membrane, which macroporous membrane has pores of sufficiently large size to avoid rate control of the drug to be transdermally delivered but to provide a thin film of a base material in use to the skin of the user;
   (c) the backing sheet and the macroporous membrane secured together to form an intermediate reservoir therebetween;
   (d) the resevoir having a composition therein comprising:
     (i) a dermatologically-acceptable, viscous liquid base material, which liquid base material comprises a hydrophilic material and is selected to exude in a controlled amount through the pores of the face membrane to form a thin film on the skin of the user and to occlude the skin of the user and to force hydration of the stratum corneum layer with water from the lower layers of the epidermic of the user in use;
     (ii) the liquid base material containing an effective, therapeutic amount of a water soluble drug for transdermal delivery, the active drug material for transdermal delivery having high solubility in the liquid base material;
   (e) a removable means to seal the face of the macroporous membrane prior to use; and
   (f) means to secure the membrane face to the skin of the user.

2. The drug delivery system of claim 1 wherein the macroporous face membrane has a pore size of about 1 to 1000 microns.

3. The drug delivery system of claim 1 wherein the liquid base material comprises a hydrophobic viscous material and the drug to be transdermally delivered comprises a hydrophobic drug.

4. The drug delivery system of claim 1 wherein the liquid base material comprises a glycerol, water-containing liquid base material and wherein the drug to be transdermally delivered comprises a water soluble drug.

5. The drug delivery system of claim 1 wherein the liquid base material comprises a viscous hydrocarbon-type material and wherein the drug to be transdermally delivered comprises a hydrophobic drug soluble in the viscous hydrocarbon liquid base material.

6. The drug delivery system of claim 1 wherein the active drug comprises a contraceptive steroid hormone.

7. The drug delivery system of claim 7 wherein the contraceptive steroid hormone is selected from the group consisting of norethindrone, norgestrel, estradiol, levonorgestrel, and mestranol and combinations thereof.

8. The drug delivery system of claim 7 wherein the liquid base material comprises a polyalkylene glycol and the drug comprises a glycol soluble steroid.

9. The transdermal drug delivery system for the delivery of a contraceptive steroid drug to the skin of a user, which system comprises:
   (a) an impervious backing sheet;
   (b) a macroporous liquid base retaining face membrane having a pore size of from about 1 to 1000 microns and pores of sufficiently large size to avoid rate control of the contraceptive hormone to be transdermally delivered by the drug delivery system;
   (c) the backing sheet and the macroporous membrane sheet secured together to form an intermediate reservoir therebetween;
   (d) means to seal the face of the macroporous face membrane prior to use, said means being easily removable by the user prior to use;
   (e) adhesive securing means about the periphery of the macroporous face membrane to permit the macroporous face membrane to be placed in contact with the skin of the user after removal of the protective means;

(f) the reservoir having a composition comprising:
  (i) dermatologically-acceptable, polyalkylene polyol liquid base material to exude in a controlled amount through the pores of the face membrane to form a thin film on the skin of the user and to occlude the skin of the user and force hydration of the stratum corneum layer with water from the lower layers of the epidermis of the user;
  (ii) the liquid base material containing an effective, therapeutic amount of a contraceptive steroid drug for transdermal delivery to the user, the steroid characterized by having a high solubility in the liquid base material;

whereby, on application to the skin of a user of the liquid drug delivery system, the liquid base material exuded from the macroporous face membrane forms a thermodynamically stable, thin film on intimate contact with the skin of the user while the steroid hormone is released through the liquid base material directly into the skin of the user.

10. A method for the transdermal delivery of a drug to a user which method comprises:
  (a) preparing a composition which comprises:
    (i) a viscous, film-forming, hydrophilic liquid base material selected to occlude the skin of the user and to force hydration of the stratum corneum layer with water from the lower layers of the epidermis of the user in use; and
    (ii) the liquid base material containing a highly soluble drug in an amount to provide an effective therapeutic amount of the drug to the user in a predetermined release pattern; and
  (b) applying a layer of the composition to the skin of the user.

11. The method of claim 10 wherein the liquid base material comprises a viscous hydrocarbon and the drug comprises a water insoluble drug.

12. The method of claim 10 wherein the liquid base material is a viscous hydrocarbon and the drug comprises a hydrocarbon soluble contraceptive steroid.

13. The method of claim 12 wherein the steroid comprises levonorgestrel, estradiol, and admixtures thereof.

14. The method of claim 10 which includes retaining the composition within a reservoir which includes a macroporous membrane and forming a thin layer of the liquid base material on the skin of the user by passing the liquid base material through the macroporous membrane.

15. The method of claim 10 wherein the liquid base material comprises a polyalkylene glycol and the drug is a glycol soluble steroid.

16. A method for the transdermal delivery of a drug from a reservoir containing the drug, which method comprises:
  (a) providing a transdermal delivery system which includes a reservoir and a macroporous face membrane, the reservoir containing a dermatologically-acceptable, viscous liquid base material selected to occlude the skin of the user and to force hydration of the stratum corneum layer of the user with water from the lower layers of the epidermis of the user, which liquid base material comprises a polyalkylene glycol containing an effective, therapeutic amount of a drug for transdermal delivery to the user, the reservoir having one face formed of a macroporous face membrane material;
  (b) placing the macroporous face membrane material adjacent to the skin of the user so as to permit the liquid base material to exude from the face membrane and to form a thin, thermodynamically stable thin film of the liquid base material on the skin of the user and in intimate contact with the thin film, and the liquid base material in the reservoir; and
  (c) introducing the drug from the liquid base material and through the thin liquid film into the skin.

17. The method of claim 9 wherein the liquid base material comprises a viscous polyethylene or polypropylene glycol and wherein the drug to be transdermally delivered comprises a glycol soluble steroid drug soluble in the liquid base material.

18. The method of claim 9 wherein the active drug comprises a contraceptive steroid hormone and wherein the contraceptive steroid hormone comprises norethindrone, norgestrel, estradiol, levonorgestrel, and mestranol and combinations thereof.

* * * * *

UNITED STATES PATENT AND TRADEMARK OFFICE
CERTIFICATE OF CORRECTION

PATENT NO. : 4,810,499

DATED : March 7, 1989

INVENTOR(S) : Elie S. Nuwayser

It is certified that error appears in the above-identified patent and that said Letters Patent is hereby corrected as shown below:

Column 10, line 42, after "claim" delete "7" and insert --6--.

Column 11, line 37, delete "predertermined" and insert --predetermined--.

Signed and Sealed this

Twenty-ninth Day of August, 1989

Attest:

DONALD J. QUIGG

Attesting Officer

Commissioner of Patents and Trademarks